United States Patent [19]  [11] 3,953,490
Shuman  [45] Apr. 27, 1976

[54] PREPARATION OF (3-TRIFLUOROMETHYLPHENOXY)(4-CHLOROPHENYL)ACETONITRILE

[75] Inventor: Richard F. Shuman, Westfield, N.J.

[73] Assignee: Merck & Co., Inc., Rahway, N.J.

[22] Filed: Nov. 12, 1974

[21] Appl. No.: 523,102

Related U.S. Application Data

[62] Division of Ser. No. 271,444, July 13, 1972, abandoned.

[52] U.S. Cl............ 260/465 F; 260/453 R; 260/473 G; 424/308
[51] Int. Cl.² ............................ C07C 121/66
[58] Field of Search......................... 260/465 F

[56] References Cited
UNITED STATES PATENTS
3,816,446    6/1974    Bolhofer .................. 260/465 X OTHER PUBLICATIONS
Asthana et al.: Indian J. Chem., Vol. 8, pp. 1086–1095 (1970).

Primary Examiner—Lewis Gotts
Assistant Examiner—Dolph H. Torrence
Attorney, Agent, or Firm—Richard A. Thompson; J. Jerome Behan

[57] ABSTRACT

A method for preparing 2-acetamidoethyl (3-trifluoromethylphenoxy)(4-chlorophenyl)acetate which comprises treating (3-trifluoromethylphenoxy)(4-chlorophenyl)acetonitrile with 2-acetamidoethanol in the presence of an acid to form an imino intermediate which, upon treatment with an aqueous solution, affords the desired product. 2-Acetamidoethyl (3-trifluoromethylphenoxy)(4-chlorophenyl)acetate is a hypocholesterolemic and hypolipemic agent which effectively reduces the concentration of cholesterol, triglycerides and other lipids in blood serum.

3 Claims, No Drawings

PREPARATION OF (3-TRIFLUOROMETHYLPHENOXY)(4-CHLOROPHENYL)ACETONITRILE

This application is a division of Ser. No. 271,444, which was filed July 13, 1972 and abandoned Nov. 24, 1974.

This invention relates to a novel method for the preparation of 2-acetamidoethyl (3-trifluoromethylphenoxy)(4-chlorophenyl)acetate.

There is no clear agreement about the actual role of cholesterol and triglycerides in the localization of atherosclerotic plaques but numerous studies support the concept that cholesterol and triglycerides play a major role in the pathogenesis of atherosclerosis because along with other lipids and fibrin they accumulate in the arterial intima and subintima and produce arterial corrosion.

It is the purpose of this invention to describe a novel method for the preparation of 2-acetamidoethyl (3-trifluoromethylphenoxy)(4-chlorophenyl)acetate which product has proved effective in reducing the concentration of cholesterol, triglycerides and other lipids in blood serum. This compound induces a significant reduction in cholesterol and triglyceride levels in serum and it achieves this result with little or no irritation to the gastrointestinal tract.

An object of this invention is to describe a novel process for the preparation of 2-acetamidoethyl (3-trifluoromethylphenoxy)(4-chlorophenyl)acetate (I).

The novel process comprises treating (3-trifluoromethylphenoxy)(4-chlorophenyl)acetonitrile (III) with 2-acetamidoethanol in the presence of an acid, for example, hydrogen chloride, p-toluenesulfonic acid, boron trifluoride and the like to afford th 2-acetamidoethyl (3-trifluoromethylphenoxy)(4-chlorophenyl)iminoacetate salt intermediate (II). This intermediate, II, may be converted to its free base; however, it has been found convenient not to isolate the salt intermediate but to treat said intermediate directly with an aqueous solution to afford 2-acetamidoethyl (3-trifluoromethylphenoxy)(4-chlorophenyl)acetate (I). The reaction may be conducted at a temperature in the range of from about −20°C. to about 30°C. In general, the reaction with the acid is conducted at a temperature in the range of from about −10°C. to about 0°C. The initial reaction with the acid is conducted employing anhydrous solvents which are inert or substantially inert to the reactants employed. Examples of solvents which may be employed include dimethylformamide, dichloromethane, dimethylacetamide, xylene and the like. The imino ester obtained is then treated with an aqueous solution to afford the desired product. The following equation illustrates this process employing hydrogen chloride as the acid; however, it should be understood that other functionally equivalent acids such as those defined above may also be employed in an otherwise similar process to afford an identical product (I):

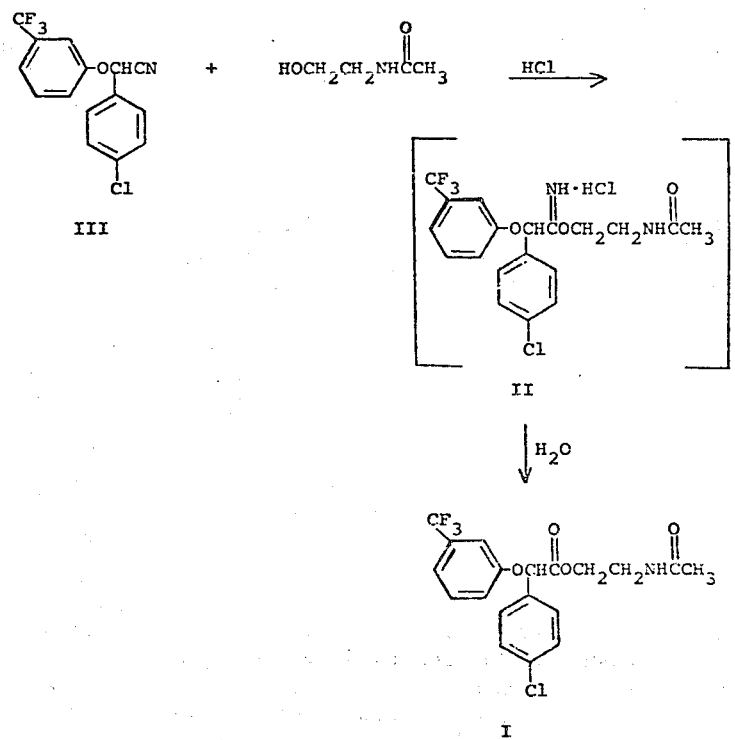

2-Acetamidoethyl (3-trifluoromethylphenoxy)(4-chlorophenyl)acetate is a crystalline solid which can be purified by recrystallizatioon from a single solvent or from a mixture of solvents, for example, by recrystallization from a lower alkanol such as methanol, ethanol, isopropanol and the like or from a mixture of these lower alkanols. Also, the product may be recrystallized from a mixture of toluene and hexane.

The (3-trifluoromethylphenoxy)(4-chlorophenyl)acetonitrile employed above is prepared by treating 4-chlorophenyl-α-haloacetonitrile with 3-trifluoromethylphenol in the presence of a base, for example, an alkali metal or alkaline earth metal base such as an alkali metal or alkaline earth metal, alkoxide, carbonate, bicarbonate or hydroxide such as potassium carbonate, calcium carbonate, sodium bicarbonate, potassium bicarbonate, sodium methoxide, potassium methoxide, sodium hydroxide, potassium hydroxide or calcium hydroxide.

The choice of a solvent is not critical to the reaction and, in general, the process may be conducted in any suitably inert medium in which the reactants are reasonably soluble. However, the base employed does not have to be appreciably soluble for the reaction to proceed. Suitable solvents include, for example, tetrahydrofuran, methylene chloride or hydrocarbons of the aliphatic, acyclic and aromatic variety which are pentane, hexane, decane, dodecane, cyclohexane, benzene, toluene, xylene and the like or alkanols, for example, lower alkanols such as methanol, ethanol and the like. Also, the process may be conducted at ambient temperatures but, in practice, the reaction is facilitated by the application of heat. In general, it is most desirable to employ temperatures in the range of from about 40°C. up to the reflux temperature of the reaction mixture over an extended period of from about one to twenty hours. The following equation illustrates this process:

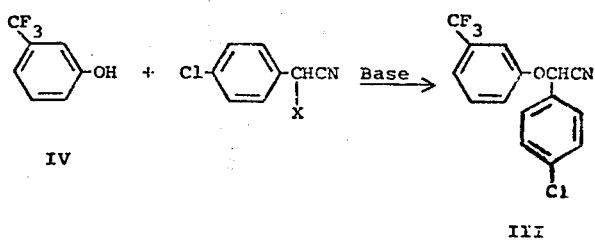

IV    III wherein X is halo such as bromo or chloro.

The 4-chlorophenyl-α-haloacetonitrile employed above may be prepared by treating 4-chlorophenylacetonitrile with a halogenating agent such as bromine, chlorine and the like under standard halogenating conditions to afford the desired product.

The following example illustrates the process of this invention. However, the examples are illustrative only and this invention should not be construed as being limited thereto since other reaction conditions and other functionally equivalent reagents may be substituted therefor to afford an identical 2-acetamidoethyl (3-trifluoromethylphenoxy)(4-chlorophenyl)acetate product.

EXAMPLE 1

2-Acetamidoethyl (3-trifluoromethylphenoxy)(4-chlorophenyl)Acetate

Step A: 4-Chlorophenyl-α-bromoacetonitrile

4-Chlorophenylacetonitrile (303.2 g., 2.0 mole) is heated to 90°C. on a steam bath and 48% hydrobromic acid (5drops) is added. Bromine (336 g., 2.1 mole) is then added dropwise to the stirred melt over a 1-hour period at 90°–95°C. The reaction mixture is heated an additional 15 minutes and then cooled. Benzene (300 ml.) is then added and 100 ml. of the benzene is removed by distillation at 80°C. The solution is cooled, filtered and the benzene removed to afford 435.5 g. of crude product which is extracted with 3 liters of hexane at 50°–55°C. Isopropanol (100 ml.) is added to the hexane solution which is then cooled to 25°C. The product is collected by filtration to afford 235.2 g. (57% yield) of 4-chlorophenyl-α-bromoacetonitrile, m.p. 46°–49°C.

Step B: (3-Trifluoromethylphenoxy)(4-chlorophenyl)Acetonitrile

To a solution of 3-trifluoromethylphenol (16.2 g., 0.1 mole) and 4-chlorophenyl-α-bromoacetonitrile (23.05 g., 0.1 mole) in methylene chloride (200 ml.) is added potassium carbonate (27.6 g., 0.2 mole). The reaction mixture is stirred and heated under reflux for six hours. The reaction mixture is then cooled to 25°C. and washed with water (300 ml.). The organic layer is dried over sodium sulfate, filtered and the solvent removed to afford crude (3-trifluoromethylphenoxy)(4-chlorophenyl)acetonitrile which is employed in the next step without further purification.

Step C: 2-Acetamidoethyl (3-trifluoromethylphenoxy)(4-chlorophenyl)acetate (3-Trifluoromethylphenoxy)(4-chlorophenyl)acetonitrile is added to a solution of 2-acetamidoethanol (20.6 g., 0.2 mole) in anhydrous dimethylformamide (25 ml.). The reaction mixture is cooled to −10°C. and saturated with hydrogen chloride (50 g., 1.37 mole) and stirred for 5 hours at −10° to 0°C. To this reaction mixture containing 2-acetamidoethyl (3-trifluoromethylphenoxy)(4-chlorophenyl)iminoacetate hydrochloride is added methylene chloride (200 ml.) and then water (100 ml.). The organic layer is collected, washed with water (2 × 100 ml.) and then dried over magnesium sulfate. The dried solution is decolorized with carbon, filtered and then slowly diluted with hexane (1 liter) to afford 10.7 g. (25% yield) of 2-acetamidoethyl (3-trifluoromethylphenoxy)(4-chlorophenyl)acetate, m.p. 93°–95°C.

I claim:

1. A process for preparing (3-trifluoromethylphenoxy)(4-chlorophenyl)acetonitrile which comprises treating 4-chlorophenyl-α-haloacetonitrile with trifluoromethylphenol in the presence of a base.

2. The process of claim 1 wherein the base is an alkali metal or alkaline earth metal base.

3. The process of claim 2 wherein the base is an alkali metal or alkaline earth metal alkoxide, carbonate, bicarbonate or hydroxide.

* * * * *